(12) United States Patent
Ionita-Manzatu et al.

(10) Patent No.: US 7,323,198 B2
(45) Date of Patent: Jan. 29, 2008

(54) ANTIOXIDANTS IN CLUSTERS OF STRUCTURED WATER

(75) Inventors: Vasile Ionita-Manzatu, Old Bethpage, NY (US); Mirela Ionita-Manzatu, Old Bethpage, NY (US); Gheorghe Cicoa, Lake Grove, NY (US); Andrew J. Bevacqua, East Setauket, NY (US)

(73) Assignee: Color Access, Inc., Melville, NY (US)

( * ) Notice: Subject to any disclaimer, the term of this patent is extended or adjusted under 35 U.S.C. 154(b) by 351 days.

(21) Appl. No.: 11/190,567

(22) Filed: Jul. 27, 2005

(65) Prior Publication Data
US 2006/0003017 A1 Jan. 5, 2006

Related U.S. Application Data

(62) Division of application No. 10/183,819, filed on Jun. 27, 2002, now Pat. No. 6,958,163.

(51) Int. Cl.
*A61K 36/82* (2006.01)
*A61K 36/53* (2006.01)
*A61K 36/16* (2006.01)
*A61K 36/00* (2006.01)
*A61K 6/00* (2006.01)

(52) U.S. Cl. ............ 424/729; 424/745; 424/752; 424/725; 424/401

(58) Field of Classification Search ............ None
See application file for complete search history.

(56) References Cited

U.S. PATENT DOCUMENTS

| 5,736,027 | A | | 4/1998 | Nakamura |
| 5,846,397 | A | | 12/1998 | Manzatu et al. |
| 5,872,089 | A | * | 2/1999 | Lo ............... 510/247 |
| 5,965,151 | A | * | 10/1999 | Manzatu et al. ...... 424/423 |
| 6,139,855 | A | * | 10/2000 | Cioca et al. ......... 424/401 |
| 6,231,874 | B1 | * | 5/2001 | Cioca et al. ......... 424/401 |
| 6,451,328 | B1 | * | 9/2002 | Ionita-Manzatu et al. ... 424/401 |
| 6,905,523 | B2 | * | 6/2005 | Vainshelboim et al. ....... 8/405 |
| 6,958,163 | B2 | * | 10/2005 | Ionita-Manzatu et al. ... 424/729 |
| 2007/0187327 | A1 | * | 8/2007 | George et al. ......... 210/639 |

FOREIGN PATENT DOCUMENTS

| EP | 0 826 636 | 3/1998 |
| EP | 1 162 176 | 12/2001 |
| GB | 2 335 142 | 9/1999 |
| RO | 107544 | 3/1996 |
| RO | 107545 | 3/1996 |
| RO | 107546 | 3/1996 |

OTHER PUBLICATIONS

Manzatu et al. Roum. Biotechnol. Lett. 1999. vol. 4, No. 1, pp. 43-51, CAPLUS Abstract enclosed.*
Stillinger, F.H., "Water Revisited", Science, vol. 209, No. 4455, pp. 451 to 457 (1980).
Shirahata,et al., "Electro-Reduc Wtr Scavenges Act Oxygen Species & Prots DNA from Oxidative Dmge", Biochem & Biophys Rrch Comm, vol. 234, No. 1,(1997) pp. 269-274, XP000978700.

* cited by examiner

*Primary Examiner*—Christopher R. Tate
(74) *Attorney, Agent, or Firm*—Yongzhi Yang

(57) ABSTRACT

The invention relates to structured water and its antioxidant activity. In addition, the present invention relates to antioxidants incorporated within the cluster structure of either electropositive (S water) or electronegative (I water). The structured water, having the antioxidant within its cluster structure, has a stabilizing effect on the antioxidant. In addition, the antioxidant activity inherent to structured water is enhanced by the presence of the antioxidant within its cluster structure. The present invention also includes methods of removing or reducing free radicals on the skin and thereby preventing the signs of skin aging and the risks of cancer associated with the presence of free radicals in the skin.

5 Claims, 2 Drawing Sheets

ANTIOXIDANTS IN CLUSTERS OF STRUCTURED WATER

The present application is a divisional of Ser. No. 10/183,819, filed Jun. 27, 2002 now U.S. Pat. No. 6,958,163, hereby incorporated by reference in its entirety.

FIELD OF THE INVENTION

The present invention relates to structured water and compositions containing structured water. In particular, the invention relates to antioxidants within the cluster structures of structured water, and the inherent antioxidant activity of structured water enhanced by the presence of an antioxidant within its cluster structure.

BACKGROUND OF THE INVENTION

Many have speculated on how water interacts with cellular components, and authors have postulated that water may in fact change structure and function once it enters into tissues and cells (see, e.g., Stillinger, "Water Revisited", Science 209, no. 4455, pp. 451-457 (1980)). Taking this theory into consideration, it is understandable that the use of I and S structured waters in compositions has been growing. For example, several oil-in-water emulsions are disclosed in RO 107546, RO 107545, and RO 107544 using structured water. These compositions relate to the use of structured water in specific cosmetic products, for the treatment of oily skin, dry skin, or acne.

Different biological properties have been suggested for the two types of structured water. S water is said to have a stimulatory effect on enzymatic and other biosynthetic processes; whereas, I water is said to be inhibitory of the same processes. Substantial differences are found among the UV spectra of I, S, tap and deionized waters, particularly in the 200 to 250 nm band. When their reactivities are measured in an electronographic field, I, S and tap waters also show significant differences. In particular, with respect to tap water, the total light flux emitted after electronographic stimulation with a positive impulse, $I^+$, is substantially equivalent to its negative impulse, $I^-$. For structured water, on the other hand, S water stimulated in the same way exhibits a very high light reactivity to a positive impulse, while its reactivity to a negative impulse is almost equivalent to that of distilled water, yielding a positive to negative ratio of greater than 1. In addition, I water samples show a high light reactivity to a negative impulse, with reactivity to a positive impulse approximately equivalent to distilled water, and having a ratio of positive to negative less than 1.

Active agents are commonly added, as separate and individual components, to compositions to impart a particular function on a target. The antioxidant is a particular active agent known to prevent the harmful effects caused by reactive oxygen species or oxidants. Reactive oxidants affect virtually all aspects of biological life by reacting with and modifying structural and functional cell systems. In biological systems, the free radical reaction is controlled by complex enzymatic and non-enzymatic defense and repair systems. Oxidative injury can occur when the antioxidant defense system does not prevent, intercept, and repair impaired processes. Such injuries can be harmful to organs such as the skin which is particularly vulnerable due to its extensive exposure to harmful visible and ultraviolet irradiation and high oxygen concentrations, and due to the presence of structures in the skin which are critical for maintaining cellular homeostasis, but which are susceptible to degradation due to oxidation.

In particular, there are four types of reactive oxygen species, superoxide, hydrogen peroxide, hydroxyl radical and singlet-oxygen which pose a threat to the skin. Superoxide radicals are produced by adding one electron to an oxygen molecule, and are formed by ultraviolet radiation and enzymatic reactions. Reactions with other superoxide radicals produce hydrogen peroxide, and some cells make hydrogen peroxide. Hydrogen peroxide is a byproduct of superoxide radical destruction and functions as a germicide, a desirable result. Hydrogen peroxide is not in and of itself a powerful oxidant, however, it is of concern because it can diffuse rapidly, and it can cross both cell membranes and nuclear membranes. Of greater concern, as it pertains to hydrogen peroxide, is its conversion to hydroxyl radicals, the greatest oxidative threat to cells. This conversion occurs quickly and easily in the presence of iron. Finally, the singlet oxygen is produced when oxygen molecules are irradiated by ultraviolet light to an excited state. In this state, one of the unpaired electrons is elevated to a higher energy level and is capable of attacking double bonds of fatty tissue.

Because of the destructive nature of oxidants, biological active agents like antioxidants are used to prevent this damage. Many topically applied products, especially those used for skin care, contain antioxidants such as for example, beta carotene, tocopherol, green tea extract, BHT, ascorbic acid and the like. However, like other biological active agents and like the targets they are intended to protect, antioxidants are vulnerable. Antioxidants can be unstable and lose their activity. In addition, as a result of their instability, other undesirable effects may be experienced in compositions containing them. For example, when antioxidants degrade, they may change color or develop an odor. Thus, there is a need to stabilize antioxidants against destabilizing factors such as, for example, light, oxygen, pH and temperature. In addition, there may be a desire to use lower amounts of antioxidants in a composition, for example, to achieve cost savings or to prevent minor irritation which may be experienced with sensitive skin. There is further a need to maximize the effectiveness of the antioxidant while minimizing the amount of the antioxidant used.

In UK Patent Application GB 2335142, I and S waters are described as being able to enhance the level of certain types of actives, including an antioxidant. This result has been observed with materials of very distinct chemical identity and biological activity, particularly, caffeine as an anti-irritant, and BHT as an antioxidant. However, these biological actives are in simple admixture with the structured water (i.e., the active is added to the structured water, but is separate from the cluster structures of the structured water). Structured water has not been known to have antioxidant activity either inherently or enhanced by the presence of the antioxidant integrated within its cluster structure. Further, antioxidants have not been known to be stabilized within the cluster structure of structured water. Furthermore, their use in cosmetic or pharmaceutical compositions has not been previously been disclosed. It has now surprisingly been discovered that structured water has inherent antioxidant activity and that incorporation of an antioxidant inside of cluster structures of structured water can be achieved and can have a beneficial stabilizing effect on the antioxidant.

SUMMARY OF THE INVENTION

The present invention relates to structured water comprising at least one cluster structure and at least one antioxidant agent within the cluster structure, and compositions containing the structured water of the present invention. The antioxidant arranged within the cluster structure of structured water is stabilized and the inherent antioxidant activity of structured water is enhanced. The structured water of the present invention, either the structured water itself or having the antioxidant in its cluster structure, can be added to cosmetic or pharmaceutical compositions in an antioxidant effective amount.

The antioxidant is integrated in a cluster structure of structured water by feeding a solution of unstructured feed water containing the antioxidant through a device for producing structured water. The antioxidant is added to the feed water before the structured water is produced. Supplying the combined antioxidant and feed water through the device causes the feed water to divide into fractions of clusters which form the cluster structures of the structured water. The antioxidant is integrated within the cluster structures.

The present invention also includes a method of stabilizing the antioxidant agent as the antioxidant is protected inside of the cluster structures of the structured water. Further, a method of reducing free radicals from the skin and the skin surface by topically applying to the skin the compositions of the present invention is provided. Because of the ability to remove free radicals, the structured water compositions of the present invention also aid in reducing the signs of aging and reducing the risk of cancer related to the presence of free radicals in the tissue of the skin, and the compositions aid in preventing or reducing free radical formation in a cosmetic or pharmaceutical formula.

DETAILED DESCRIPTION OF THE INVENTION

Figure 1:
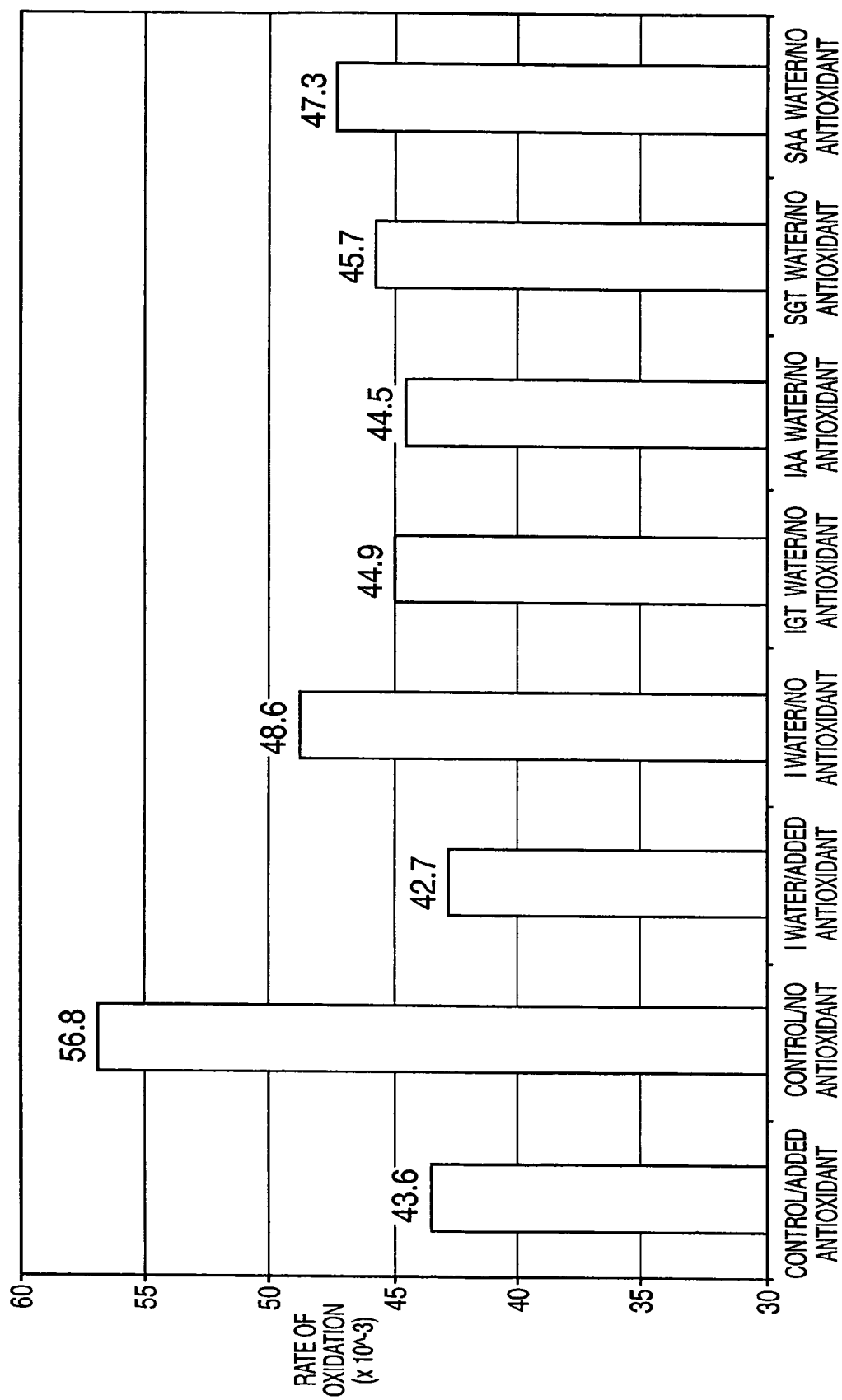
FIG. 1 is a bar chart depicting the antioxidant activity of samples of lotion containing various types of water; specifically, the Control/added antioxidant and the Control/no antioxidant samples contain distilled water, the I Water/added antioxidant and the I Water/no antioxidant samples contain I Water, the IGT Water/no antioxidant sample contains I water with green tea within its cluster structure, the IAA Water/no antioxidant sample contains I water with ascorbic acid within its cluster structure, the SGT Water/no antioxidant sample contains S water with green tea within its cluster structure, and the SAA Water/no antioxidant contains S water with ascorbic acid within its cluster structure.

It has now been discovered that structured water possesses antioxidant activity and that an antioxidant agent can be incorporated within its cluster structure providing stability to the antioxidant and enhancing the antioxidant activity of the structured water. As noted above, structured water is known in the art. In particular, I and S waters are derived from feed water which has conductivity, C (µS/cm), of about 250 to 450, and a pH of about 5.0 to 7.5. Interaction of the dipolar molecular structure of tap water with an electrical field simultaneously produces I and S water. The conductivity of I water is characterized by C (µS/cm) of about 500 to 3500, and a pH of about 2.0 to 4.0; and the conductivity of S water is characterized by C (µS/cm) of about 600 to 2500, and a pH of about 10.0 to 12.0.

The present invention includes methods of making structured water having the antioxidant within its cluster structure. The process of making structured water is described for example, in RO 88053 which describes a method for producing "B" or basic (S-type) water, and RO 88054 which discloses a method for making "A" or acid (I-type) water. The content of each of these documents is incorporated herein by reference. One specific method of preparing I and S waters generally is disclosed in U.S. Pat. No. 5,846,397 and is incorporated herein by reference.

Feed water used to make the structured water of the present invention comprises an ionic component having certain concentrations of anions and cations. Specifically, the feed water is prepared with an ionic component of extremely small concentrations of cations and anions such as, for example, $CaCl_2$, $MgCl_2$, $Na_2SO_4$, $KH_2PO_4$, and $KNO_3$. The range of concentrations of ions in the ionic component can be, for example, $CaCl_2$ in an amount of about 8.00 to 15.00 mg/100 ml of the feed water, $MgCl_2$ in an amount of about 2.00 to 6.00 mg/100 ml, $Na_2SO_4$ in an amount of about 6.00 to 12.00 mg/100 ml, $KH_2PO_4$ in an amount of about 0.200 to about 1.000 mg/100 ml, and $KNO_3$ in an amount of about 0.80 to 1.20 mg/100 ml. Specifically, for example, to make I water and S water, generally, the ion content of the ionic component can be 10.85 mg/100 ml $CaCl_2$, 4.25 mg/100 ml $MgCl_2$, 9.25 mg/100 ml. $Na_2SO_4$, 0.70 mg/100 ml $KH_2PO_4$, and 1.05 mg/100 ml $KNO_3$. These amounts are weighed on an analytical or micro balance sensitive to a number of decimal places greater than 3. To make I water and S water with the antioxidant in their cluster structure, generally, the ion content of the ionic component can be, for example, 10.00 mg/100 ml $CaCl_2$, 3.75 mg/100 ml $MgCl_2$, 8.80 mg/100 ml $Na_2SO_4$, 0.60 mg/100 ml $KH_2PO_4$, and 1.00 mg/100 ml $KNO_3$.

The structured water making device uses one or several serial structuring cells placed in a chemically inert parallelipipedic column made out of glass or plexiglass, for example. The cells are typically supported on four legs and are enclosed on top by a cover, but other means of support and enclosure can be used. Each structuring cell has a pair of activators and numerous working spaces. The working spaces are generally arranged such that there are two working spaces available to supply feed water, two working spaces each for generating, and for gathering and disposing S water, and two working spaces each for generating, and for gathering and disposing I water. In the space for generating or producing the S water, the polarization and energy needed for binding water molecules, by hydrogen and hydroxyl bridges, in polymolecular aggregates with radicals ($R^+$), are present as a result of the electrostatic field being about 60 to 120 V. Similarly, polymolecular aggregates with radicals ($R^-$) are simultaneously formed to make I water, in the space for producing I water.

The activators are made of two inox stainless (e.g., stainless steel) lamellar electrodes located on each side of, or formed by, two porous membranes which are chemically inert, and therefore, resistant to solutions having a pH between about 2.0 to 14.0. The space between the two porous membranes provides space through which the feed water can pass. The two porous membranes of the activators are held tightly in place by a gasket in the parallelipipedic column. The positive electrode is in the space for gathering and disposing the I water and the negative electrode is in the space for gathering and disposing the S water.

To integrate the antioxidant in the cluster structure of structured water, feed water containing the antioxidant is fed through the parallelipipedic column in a volume, for example, of about 80 to 320 L, at a flow rate of about 100 to 350 L/hour to make structured water having inherent antioxidant activity. The concentration of the antioxidant in the unstructured feed water is about 0.01 mg/100 ml to about 20 mg/100 ml, preferably 1 mg/100 ml to 10 mg/100 ml, and more preferably about 1 mg/100 ml to 5 mg/100 ml.

The concentration of the antioxidant in the feed water, and the concentration of cations and anions in the feed water used to produce the structured water affects the stability of the antioxidant within the cluster structure of structured water. If the amount of antioxidant is too great, the antioxidant will precipitate out of the cluster. When using green tea as the antioxidant, for example, discoloration will occur especially in S water because it is basic.

Structured water contains electronegative and electropositive clusters of water molecules stabilized by ions. Each of these two types of clusters, present in water, is commonly referred to as "I water" and "S water". On the one hand, I water contains electronegative clusters of water molecules stabilized by ions which can be characterized as being $R_m^+R_k^-(H^+)_n(H_2O)_l$, where k>>m, and conversely, on the other hand, S water contains electropositive clusters of water molecules stabilized by ions which can be characterized as being $R_k^-R_m^+H_n^+(OH^-)_p(H_2O)_l$, where k<<m. In each case of I water and S water, $R_m^+$ mainly include, but are not limited to, $Ca^+$, $Mg^+$, $Na^+$, $K^+$ cations, and $R_k^-$ ions mainly include, but are not limited to, $Cl^-$, $H_2PO_4^-$, $SO_4^-$ anions.

In one embodiment of the present invention, the antioxidant agent is integrated within the cluster structures of I water or S water. To prevent the undesired effects experienced when antioxidants lose their activity, the present invention provides protection against destabilizing factors by nestling the antioxidant within the cluster structures of structured water. Specifically, structured water having an antioxidant in its cluster structure is surprisingly stable against pH, temperature, light, and/or oxygen exposure, conditions which typically cause the antioxidant to degrade. The cluster structure of the structured water is very stable. While not wishing to be bound by any particular theory, it is believed that additional ions are introduced into the system of cluster structures by replacing the ion which stabilizes the structure with ions that have the same or similar ionic radius. In addition, when the antioxidant is intrinsic within the cluster structure of structured water, the inherent antioxidant activity of structured water is fortified.

The antioxidant incorporated within the cluster structure of structured water preferably has a large negative electrical charge, large mass, and large ionic radius. These characteristics determine the concentration of antioxidant which can be incorporated in the cluster structure of structured water. Antioxidants that are neutral are also included within the scope of the present invention. The cluster structures of structured water form around the neutral antioxidant, as well as other antioxidants, and in effect hold the antioxidant-inside the formed cluster structure. The type of antioxidant incorporated within the network of the cluster structure can be any water soluble antioxidant which is beneficially used in a topical cosmetic or pharmaceutical composition. Examples of suitable antioxidants include, but are not limited to, ginkgo-biloba, beta carotene, green tea, ascorbic acid and derivatives thereof such as for example sodium ascorbyl phosphate and magnesium ascorbyl phosphate, carnosic acid (rosemary), and BHT and BHA. The green tea, as well as other antioxidants, can be in the form of an extract or any other known form of the antioxidant, as well as the active components of extracts, e.g., catechin based flavonoids such as EGCG (epigallcatechin gallate) from green tea, rosemary extract, and the like. The antioxidant has a dipolar molecular structure associated with its electrical charge. The antioxidant of the present invention is preferably one that is labile because one of the surprising benefits of the present invention is the ability to stabilize labile antioxidants when they are present within the cluster structure of structured water.

The structured water of the present invention can also be used to provide antioxidant activity in any topical or non-topical cosmetic or pharmaceutical product in which there is an aqueous component. Structured I or S water, alone or having the antioxidant within its cluster structure, can constitute the entire aqueous component of the composition. When structured water alone is used as the aqueous component in a cosmetic or pharmaceutical composition in antioxidant effective amounts, it is preferably from about 1 to about 99.5% by weight of the composition as a whole, more preferably at levels of from about 20 to 80%, more preferably still from about 40 to 80%. The antioxidant effective amount of structured water having the antioxidant in its cluster structure when used in a cosmetic or pharmaceutical composition can be 0.05 to about 99.50% by weight of the composition as a whole, more preferably about 2 to 40%, and more preferably about 2 to 20%. Further, the structured water, alone or having the antioxidant in its cluster structure, can be a portion of a traditional aqueous component, i.e., it is combined with other non-structured aqueous components, such as distilled water, or floral water. The use of non-structured water with structured water is possible because of the specificity and the stability of structured water.

The structured water alone or the structured water having the antioxidant in its cluster structure can be used as a purely aqueous vehicle as part of a hydroalcoholic vehicle, or it can be used as part of the aqueous phase of any emulsion such as, for example, a water-in-oil or oil-in-water emulsion to provide antioxidant activity. The form the vehicle takes can be any which is suitable for topical application to the skin, for example, solutions, colloidal dispersions, emulsions, suspensions, creams, lotions, gels, foams, mousses, sprays and the like. For example, it can be used in skin care products, such as cleansers, toners, moisturizers, masks, scrubs, and the like, and it can be used in makeup products, such as lipsticks and glosses, foundations, blushes, eyeliners, eyeshadows and the like. It will also be useful in treatment products, including pharmaceutical products, in which the stability of the antioxidant is particularly crucial.

In another embodiment of the present invention, cosmetic or pharmaceutical compositions contain an antioxidant effective amount of structured water, either I water or S water. Use of the term "antioxidant effective amount" herein means an amount sufficient to prevent the harmful effects of reactive oxygen species comparable with other known antioxidants, such as for example 1% ascorbic acid in combination with deionized water or any other known cosmetic or pharmaceutical vehicle. The intrinsic structural properties of electronegative and electropositive clusters of I water and S water, respectively, while not wishing to be bound to any particular theory, are believed to inactivate free radicals in the skin, and when incorporated in a composition, they are believed to inactivate free radicals in the composition as well.

Other biological active agents can be added to the structured water of the present invention or to the compositions containing the structured water. The biological active agents are simply added after processing the feed water to produce the structured water or are added to compositions containing the structured water. The type of biological active agent added, can be any which is beneficially used in a topical cosmetic or pharmaceutical composition. For example, the structured water can contain within its cluster structure, moisturizing actives, agents used to treat age spots, keratoses and wrinkles, as well as analgesics, anesthetics, anti-acne agents, antibacterials, antiyeast agents, antifungal agents, antiviral agents, antidandruffagents, antidermatitis agents, antipruritic agents, antiemetics, antimotion sickness agents, anti-irritant agents, anti-inflammatory agents, antihyperkeratolytic agents, anti-dry skin agents, antiperspirants, antipsoriatic agents, antiseborrheic agents, hair conditioners and hair treatment agents, antiaging agents, antiwrinkle agents, sunscreen agents, antihistamine agents, skin lightening agents, depigmenting agents, wound-healing agents, vitamins, corticosteroids, self-tanning agents, or hormones.

The following non-limiting examples illustrate the invention.

EXAMPLES

Example I

Structured Water with Antioxidant in its Cluster Structure

The following is an example of the ionic composition of feed water containing an antioxidant for use in making structured water with the antioxidant in its cluster structure.

| Ion | Amount (mg/100 ml) |
|---|---|
| $CaCl_2 \times 6 H_2O$ | 10.00 |
| $MgCl_2 \times 6 H_2O$ | 3.73 |
| $Na_2SO_4$ | 8.80 |
| $KH_2PO_4$ | 0.60 |
| $KNO_3$ | 1.00 |
| Green Tea | 2.00 |

Feed water is prepared with the ionic composition described above by adding each ion to the feed water. After ions are added, the green tea is added to the feed water. The resulting feed water has a conductivity of about 340 to 345 μS/cm and a pH of about 5.8 to 6.3. The feed water is fed into the structured water making device at a flow rate of about 200 L/hour. The spaces for gathering and disposing the I water and S water holds a volume of about 220 L. The dipolar molecular structure of the feed water containing green tea is subjected to an electrostatic field having a voltage of about 80 V which causes the water structuring process. Negative $R_k^-$ ions and negative ionic components of green tea are in the majority and the positive $R_m^+$ ions are in the minority, and as a result of dissociation of the feed water containing the green tea, they migrate into the spaces for 1 water. The resulting I water with green tea in its cluster structure has a pH of about 2.2 to 2.6 and a conductivity of about 1500 to 3000 μS/cm. The other result of dissociation produces S water where negative $R_k^-$ ions are in the minority, and the positive $R_m^+$ ions and positive ionic components of green tea are in the majority. The resulting S water with green tea in its cluster structure has a pH of about 10.5 to 11.8 and a conductivity of about 600 to 1500 μS/cm.

Example II

The following formula is an example of a composition containing structured water of the present invention.

| Ingredient | Percent |
|---|---|
| Structured Water | 49.00 |
| Methylparaben | 0.20 |
| Butylene glycol | 4.00 |
| Polymeric quaternary ammonium salt | 12.00 |
| Octyl methoxycinnamate | 8.00 |
| Siloxane polymer | 5.00 |
| Wax | 1.50 |
| Cyclomethicone | 20.20 |
| Fragrance | 0.10 |

This example illustrates the antioxidant effect of a lotion containing structured water having antioxidant activity either inherently or by having an antioxidant agent in its cluster structure according to the present invention. The structured water of the formulation can be I water, S water, I water with antioxidant in its cluster, or S water with antioxidant in its cluster. A total of eight samples are prepared according to the formula above to demonstrate the antioxidant effect of the present invention. Four samples, I water prepared with 2 mg/100 ml green tea extract in its cluster structure (IGT Water/no antioxidant), I water prepared with 2 mg/100 ml ascorbic acid in its cluster structure (LAA Water/no antioxidant), S water prepared with 2 mg/100 ml green tea in its cluster structure (SGT Water/no antioxidant), and S water prepared with 2 mg/100 ml ascorbic acid in it cluster structure (SAA/no antioxidant) are prepared. Two additional samples are prepared where in one, the structured water component (49%) in the formula above is 45% I water, 2% green tea and 2% of an antioxidant mixture comprising various antioxidants, e.g., BHT, beta carotene, carnosol extract (rosemary), vitamin E and derivatives, and vitamin C and derivatives, added to the composition (I Water/added antioxidant), and in the other, the structured water is 49% I water (I Water/no antioxidant). The remaining two samples are deionized water (DI water) with about 4% antioxidant mixture added to the composition, and DI water without antioxidant (Control/added antioxidant and Control/no antioxidant).

To each of the eight samples, previously described, 2 mg/100 ml of green tea is added to retard the onset of oxidation in order to control the ability to analyze the antioxidant effect of each of the samples. When the process of oxidation occurs too rapidly it cannot be adequately observed and measured. The same amount is added to each sample tested such that the effect of the additional green tea is normalized.

Over a period of 24 hours, each sample is subjected to three "oxidative attacks." The first attack is made initially at the start of the experiment (t=0 hours), the second is made at 4 hours, and the third is made at 24 hours. The results, as shown in FIG. 1, indicate that at 24 hours, after the third oxidative attack, I water and S water having 2 mg/100 ml of either green tea or ascorbic acid within their cluster structures is comparable in antioxidant activity to the control sample with antioxidant in the lotion formula. Thus, it is demonstrated that structured water prepared with 2 mg/100 ml of an antioxidant in the feed water, and used in the lotion formula is stable and about as effective as about 4% (4000 mg/100 ml) antioxidant added directly to the lotion formula. The antioxidant activity of the present invention is about 100 times as effective as the same amount of the same antioxidant added to deionized water, preferably 250 times as effective, and more preferably about 500 to 2000 times as effective. Therefore, surprisingly, a comparable and desirable level of antioxidant activity can be achieved using less antioxidant with the structured water of the present invention.

When the antioxidant is present within the cluster structure of structured water, the antioxidant is stable and does not succumb to the threat of instability due to external factors. This is exhibited by the lack of color change in lotion samples containing the structured water having the antioxidant in its cluster structure and the brown color of lotion samples containing antioxidant added to the formulation.

Example III

This example illustrates the effect that electronegative and electropositive clusters of I water and S water have on the inactivation of free radicals. Fluorescence measurements are made in a structured water and lucigenin system, although any other known method of detecting reactive oxygen species can be utilized. The chemilluminiscence of lucigenin (bis-N-methylacridinium nitrate) occurs when it reacts with a reactive oxygen species. Therefore, a lower intensity of the luminescent emission indicates that free radicals were inactivated by the experimental sample solution and not present to react with lucigenin. The principle of this method is based on the reaction of superoxide ion radicals with lucigenin which produces a fluorescent compound. The intensity of the fluorescent signal is directly proportional to the amount of the superoxide ions present in the solution.

Three reactive solution mixtures are prepared containing 0.5 ml lucigenin, having a concentration of 0.5 g/100 ml, 0.25 ml NaOH 4N in distilled water, 1 ml of a mixture of 2 g/100 ml Tween 80, 4 g/100 ml EtOH, and 1 ml of hydrogen peroxide having a concentration of about 1.3 g/100 ml in solutions of one of the following types of water 1) distilled water, 2) I water, and 3) S water. A fourth solution is prepared with distilled water and 1% ascorbic acid in the previously described lucigenin system.

Figure 2:
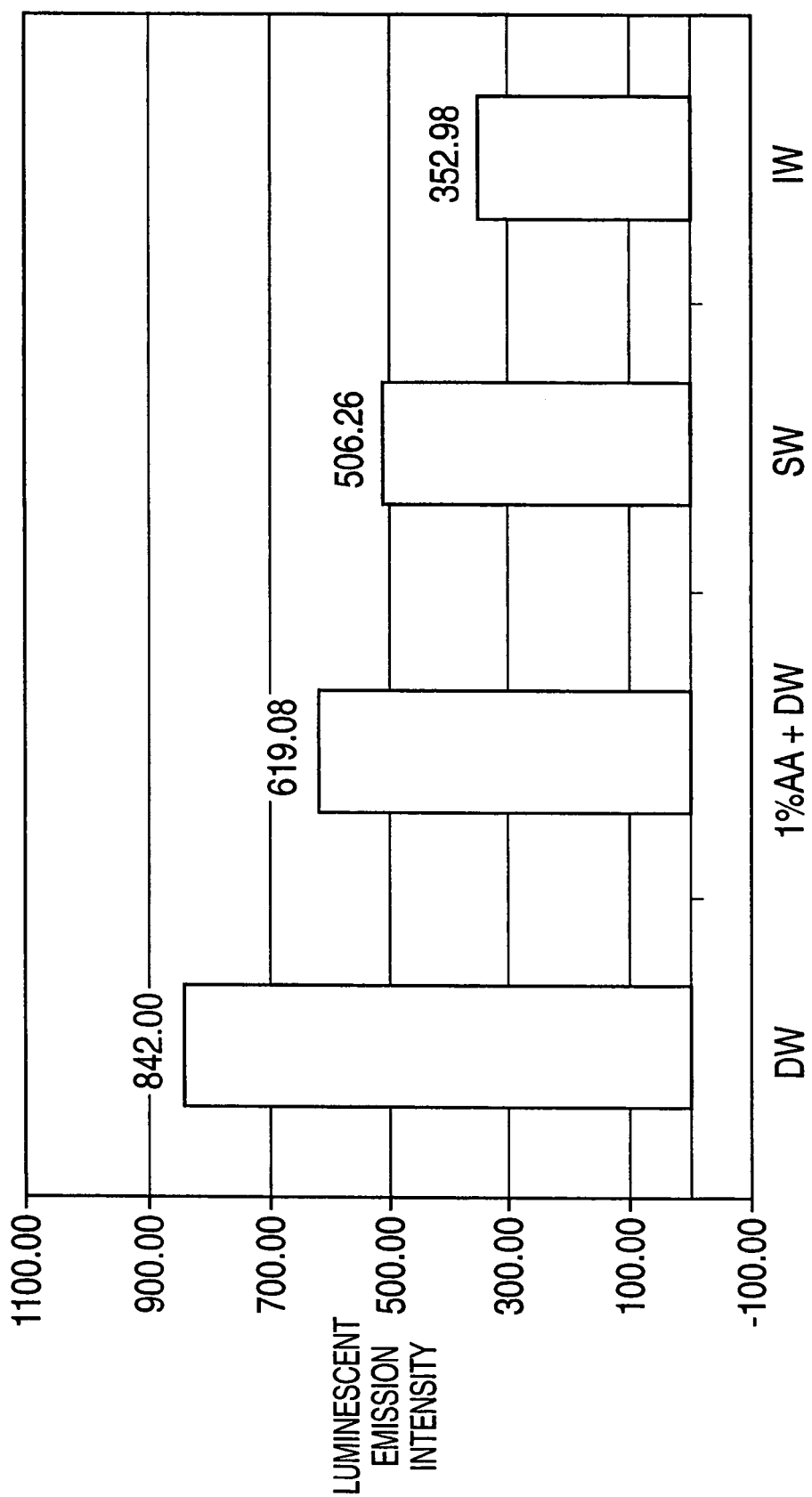
FIG. 2 is a bar chart depicting the antioxidant activity of I water and S water in comparison with deionized water alone and with 1% ascorbic acid added to it.

The results of the luminescent emission spectra of these samples, provided in FIG. 2, demonstrate that S water and I water exhibit greater antioxidant effect than distilled water containing 1% ascorbic acid. Thus, I water and S water, even without antioxidants incorporated in their clusters, exhibit antioxidant activity.

What we claim is:

1. A method of removing oxygen free radicals from the skin comprising the step of applying to the skin a structured water having at least one antioxidant agent integrated within at least one cluster structure of said structured water, said structured water comprising a combination of I and S water, wherein I water is characterized by a conductivity of about 500 to 3500, and a pH of about 2.0 to 4.0, and wherein S water is characterized by a conductivity of about 600 to 2500, and a pH of about 10.0 to 12.0.

2. The method of claim 1 wherein said antioxidant agent is water soluble.

3. The method of claim 1 wherein said cluster structure comprises electronegative aggregates of water molecules forming I water.

4. The method of claim 1 wherein said cluster structure comprises electropositive aggregates of water molecules forming S water.

5. The method of claim 1 wherein said antioxidant agent is selected from the group consisting of ginkgo-biloba extract, beta carotene and derivatives thereof, green tea extract, ascorbic acid and derivatives thereof, carnosic acid and derivatives thereof, BHT, BHA, and combinations thereof.

* * * * *